United States Patent
Ederle-Lerch et al.

(10) Patent No.: US 10,239,813 B2
(45) Date of Patent: Mar. 26, 2019

(54) METHOD FOR PRODUCING CALCIUM DIPROPIONATE

(71) Applicant: ADDCON EUROPE GMBH, Bitterfoled-Wolfen (DE)

(72) Inventors: Klaus Ederle-Lerch, Aschau im Chiemgau (DE); Norman Killian, Halle (DE); Bernd Kochannek, Bonn (DE); Hans-Jürgen Stüwe, Bad Schmiedeberg (DE)

(73) Assignee: Addcon Europe GMBH (DE)

( * ) Notice: Subject to any disclaimer, the term of this patent is extended or adjusted under 35 U.S.C. 154(b) by 0 days.

(21) Appl. No.: 15/737,645

(22) PCT Filed: Jul. 6, 2016

(86) PCT No.: PCT/EP2016/066019
§ 371 (c)(1),
(2) Date: Dec. 18, 2017

(87) PCT Pub. No.: WO2017/009151
PCT Pub. Date: Jan. 19, 2017

(65) Prior Publication Data
US 2018/0186717 A1 Jul. 5, 2018

(30) Foreign Application Priority Data

Jul. 10, 2015 (DE) .................. 10 2015 212 984

(51) Int. Cl.
| | | |
|---|---|---|
| *B01J 19/00* | (2006.01) | |
| *C07C 53/122* | (2006.01) | |
| *C07C 51/41* | (2006.01) | |
| *B01F 3/18* | (2006.01) | |
| *B01F 3/22* | (2006.01) | |

(52) U.S. Cl.
CPC .......... *C07C 51/412* (2013.01); *B01F 3/188* (2013.01); *B01F 3/223* (2013.01); *B01J 19/002* (2013.01); *B01J 19/0013* (2013.01); *C07C 53/122* (2013.01); *B01J 2219/00051* (2013.01); *B01J 2219/00162* (2013.01); *B01J 2219/00166* (2013.01)

(58) Field of Classification Search
CPC .................................................. C07C 51/412
See application file for complete search history.

(56) References Cited

U.S. PATENT DOCUMENTS

| | | |
|---|---|---|
| 4,700,000 A | 10/1987 | Merkel et al. |
| 6,986,909 B2 | 1/2006 | Van Dyck |
| 2003/0032841 A1 | 2/2003 | Dyck |
| 2005/0131249 A1* | 6/2005 | Stedman .............. C07C 51/412 562/8 |
| 2008/0317934 A1* | 12/2008 | Hauk ................... C07C 51/412 426/635 |

FOREIGN PATENT DOCUMENTS

| | | |
|---|---|---|
| DE | 32 15 752 A1 | 11/1983 |
| EP | 0 093 317 A1 | 11/1983 |
| EP | 1 072 581 A2 | 1/2001 |
| WO | 03/087028 A1 | 10/2003 |

OTHER PUBLICATIONS

International Search Report for International Application No. PCT/EP2016/066019 dated Sep. 2, 2016.

* cited by examiner

*Primary Examiner* — Paul A Zucker
(74) *Attorney, Agent, or Firm* — Seth L. Hudson; Clements Bernard Walker, PLLC

(57) ABSTRACT

The invention relates to a method for the production of calcium dipropionate by a batch process in a single pressure-resistant reaction vessel. The reaction vessel is charged with calcium oxide, calcium hydroxide, calcium carbonate or a mixture thereof. Then, pure high-concentrated propionic acid, preferably in a concentration of above 99% is added to the solid raw materials. The heat (up to 160° C.) and pressure (up to 10 bar) are retained in the reaction vessel and are subsequently used to discharge the reaction water after the complete amount of acid has been added. After a reaction time of 3 to 6 hours, pure calcium dipropionate with a water content of below 1% is obtained.

4 Claims, No Drawings

METHOD FOR PRODUCING CALCIUM DIPROPIONATE

FIELD OF THE INVENTION

The invention relates to a solid-material method for the production of calcium dipropionate.

BACKGROUND OF THE INVENTION

Calcium dipropionate, also known as calcium propionate (empirical formula $C_6H_{10}CaO_4$; CAS No. 4075-81-4) is employed worldwide on an industrial scale both as a food additive (E 282) and in the formulation of feed additives. Typically, an aqueous suspension of calcium hydroxide, either produced directly from calcium oxide through hydration through suspension of calcium hydroxide in water, is neutralized with propionic acid. After complete neutralization, the calcium dipropionate produced will dissolve in hot water and can be subjected to a clear filtration to remove impurities, followed by concentration. The separation of calcium dipropionate from the aqueous solution is achieved either through evaporation with subsequent separation of the crystals developed in a normal solid-liquid separation systems, or through spray-drying. This technology results in high purity products, but is quite expensive, not least because of the low water solubility of calcium dipropionate, the high energy requirement during the processing and the necessity of highly complex production units.

A great number of the known methods for the production of alkali and alkaline earth propionates are based on neutralizing alkali and/or alkaline earth hydroxides with propionic acid in the aqueous phase. The methods are carried out without pressure or under elevated pressure, with either anhydrous or hydrated propionic acid. DE 32 15 752 A1/EP 0 093 317 A1/U.S. Pat. No. 4,700,000 describes such a method in an exemplary way. The resulting reaction solutions are typically purified by clear filtration, again due to the moderate solubility of calcium dipropionate under elevated pressure and temperature. The separation and further processing of the produced alkali and/or alkaline earth propionates is carried out using different separation methods. In the case of calcium dipropionate, a significant amount of the currently produced product is produced by a spray-drying method from the purified calcium dipropionate solution, or from a calcium dipropionate suspension. Furthermore, the concentration by evaporation of the reaction solution and the crystallization of calcium dipropionate from the saturated solution with subsequent separation by centrifugation is very important to the currently used technologies. Further, the direct reaction of calcium oxide and/or calcium hydroxide with propionic acid in reactors without added water is also carried out. This reaction takes place exclusively in the solid phase. Problems in the removal of the reaction heat lead to local overheating, decomposition and, as a result, to color changes (graying) of the calcium dipropionate as well as to losses of propionic acid due to the azeotropes produced when the reaction is still incomplete. These problems arise from the inhomogeneous reaction control and are due to the exothermic nature of the neutralization. The quality differences that result therefrom in the commercially available calcium dipropionate products are the reason why such solid-state methods are not widely practiced.

EP 1 072 581 A2 describes a method for the production of calcium propionate, and a device for performing the process. What is described is a method for the production of calcium propionate powder using a convection dryer in which a one-part pumpable suspension of calcium propionate in water with a calcium propionate content equal to or above 30% (w/w) is supplied to a convection dryer, as well as a device for performing this process, comprising a reactor, a loop, a dispersion machine, and optionally a storage tank with a dryer.

U.S. Pat. No. 6,986,909 B2 describes an attempt to solve the problem of poor heat dissipation by applying the propionic acid on an inert inorganic carrier, which should enable a more favorable heat distribution in the subsequent reaction by adding calcium hydroxide. The inert carrier, however, remains in the end product, which would make it suitable only for application in feedstuffs.

BRIEF SUMMARY OF THE INVENTION

The object of the present invention is to provide a solid-material method for the production of calcium dipropionate, without the reaction energy released and the carbon dioxide formed when calcium carbonate is used leading to a loss of propionic acid, to very long reaction times because of problems with cooling the solids, to a lack of homogeneity of the final product as is often seen in the solid-material methods, as well as to energy losses.

In a first embodiment, the above object is achieved by a carrier-free solid-material method for the production of calcium propionate powder in a pressure-resistant solid-state mixing reactor by charging calcium oxide, calcium hydroxide or calcium carbonate or mixtures of these calcium compounds, and adding propionic acid by a reaction directly in the solid phase under a pressure that is increased above normal pressure.

DETAILED DESCRIPTION OF THE INVENTION

The present invention describes a carrier-free solid-material method in which propionic acid, under pressure in a corresponding reactor, can be reacted with mixtures of calcium oxide, calcium oxide and calcium hydroxide, calcium oxide and calcium carbonate, or the respective pure calcium compounds, to calcium dipropionate directly in the solid phase, without the reaction energy released and the carbon dioxide formed when calcium carbonate is used leading to a loss of propionic acid, to very long reaction times because of problems with cooling the solids, to a lack of homogeneity of the final product as is often seen in the solid-material methods, and to energy losses, since the reaction energy released remains in the system because of the pressure operation, and can be used directly for drying the end product after the reaction is complete.

In the solid-material methods previously used for the production of calcium dipropionate though the direct reaction of calcium oxide or mixtures of calcium oxide and calcium hydroxide with propionic acid, very efficient cooling is necessary in the initial phase in order to prevent temperature increases that lead to losses of propionic acid and product decomposition. Once the calcium oxide present in the reactor is hydrolyzed by reaction water produced, heat production is noticeably reduced. The heat produced by the neutralization of calcium hydroxide is insufficient to completely evaporate the forming reaction water in practice. Thus, the reaction control and the drying must be completed by supplying heat. Therefore, in the process according to the invention, a mixture of calcium oxide and calcium hydroxide or a mixture of calcium oxide and calcium carbonate is charged in a pressure-resistant stainless steel reactor. The stoichiometrically necessary amount of propionic acid is then metered into the reactor under intensive mixing, while the temperature and pressure increase significantly. The temperature can reach 150° C. to 180° C.; the pressure increases to from 2 to 10 bar, depending on the size ratio between the reactor volume and the amount of starting materials present in the reactor. After completion of the propionic acid addition, an afterreaction period of about 0.5 to 2 hours begins. After this, the reactor contents are depressurized in a controlled manner. Depending on the starting materials and/or their amounts, steam and/or a mixture of steam and carbon dioxide, which may still contain traces of calcium hydroxide dust or propionic acid, is released. Depending on the calculated molar ratio of calcium oxide to calcium hydroxide, or calcium oxide to calcium carbonate, the reaction can be controlled in such a manner that no additional energy must be supplied for the complete drying of the produced calcium dipropionate. A homogeneous product is obtained, which meets the usual purity requirements for calcium dipropionate for food or feed applications, and can be produced homogeneously in terms of pH and particle size distribution.

EXAMPLES

Example 1—Production of Calcium Dipropionate from Calcium Oxide and Propionic Acid In a 110 liter stainless steel reactor, 15.8 kg of calcium oxide is charged. Over a period of 4 hours, 41.7 kg of propionic acid is metered thereto. Towards the end of the addition of propionic acid, the temperature inside the reactor and the reactor pressure had to be maintained, through careful pressure release, at 180° C. and 5 bar, respectively. To complete the process, the reaction mixture remained in the reactor for a further 30 minutes. Next, with careful and controlled pressure release, the water formed in the reaction is evaporated from the reactor through a vapor precipitator. Once the reactor temperature had dropped below the dew point, the reaction product could be dried to the required water content by further heating and applying a vacuum. The resulting product was 52.1 kg of calcium dipropionate as a fine white powder with a moisture content of 1.3% by weight and a content of 0.48% by weight water-insoluble compounds. The purity of the dried product was 96.2% by weight.

Example 2—Production of Calcium Dipropionate from a Mixture of Calcium Oxide and Calcium Hydroxide with Propionic Acid In a 110 liter stainless steel reactor, 9.2 kg of calcium oxide and 8.6 kg of calcium hydroxide are charged. Over a period of 2 hours, 41.5 kg of propionic acid is metered thereto. At the end of the addition of the propionic acid, the temperature inside the reactor and the reactor pressure had increased to 180° C. and 5 bar, respectively. To complete the process, the reaction mixture remained in the reactor for a further 30 minutes. Next, with careful pressure release, the water formed in the reaction is evaporated from the reactor through a vapor precipitator. Once the reactor temperature had dropped below the dew point, the reaction product could be dried to the required water content by further heating and applying a vacuum. The resulting product was 54.0 kg of calcium dipropionate as a fine white powder. The calcium dipropionate produced had a moisture content of 1.3% by weight and a content of 0.55% by weight of water-insoluble compounds. The purity of the dried product was 96.1% by weight.

Example 3—Production of Calcium Dipropionate from a Mixture of Calcium Oxide and Calcium Carbonate with Propionic Acid In a 110 liter stainless steel reactor, 9.2 kg of calcium oxide and 11.7 kg of calcium carbonate are charged. Over a period of 2 hours, 41.5 kg of propionic acid is metered thereto. At the end of the addition of propionic acid, the temperature inside the reactor and the reactor pressure had increased to 160° C. and 3 bar, respectively. To complete the process, the reaction mixture remained in the reactor for a further 300 minutes. Next, with careful pressure release, the carbon dioxide formed in the reaction and the formed water were evaporated from the reactor through a vapor precipitator. Once the reactor temperature had dropped below the dew point, the reaction product could be dried to the required water content by further heating and applying a vacuum. The reaction product was 54 kg of calcium dipropionate as a fine white powder with a purity of 96.6% by weight, with a content of 0.4% by weight of water-insoluble compounds and a moisture content of 1.6% by weight.

Example 4—Production of Calcium Dipropionate from Calcium Carbonate and Propionic Acid In a 110 liter stainless steel reactor, 28.2 kg of ground calcium carbonate is charged. Over a period of 2 hours, 41.5 kg of propionic acid is metered thereto. At the end of the addition of propionic acid, the temperature inside the reactor and the reactor pressure had increased to 155° C. and 3 bar, respectively. To complete the process, the reaction mixture remained in the reactor for a further 360 minutes. Next, with careful pressure release, the carbon dioxide formed in the reaction and the formed reaction are evaporated through a vapor precipitator.

Once the reactor temperature had dropped under the dew point, the reaction product could be dried to the desired water content by further heating and applying a vacuum. The reaction product was 54 kg of calcium dipropionate as a fine white powder with a purity of 96.2% by weight, with a content of 0.4% by weight of water-insoluble compounds and a moisture content of 1.5% by weight.

The invention claimed is:
1. A carrier-free solid-material method for the production of powdery calcium propionate in a pressure-resistant solid-state mixing reactor by charging calcium oxide, calcium hydroxide or calcium carbonate or mixtures of these calcium compounds, and adding propionic acid by a reaction directly in the solid phase under a pressure that is increased above normal pressure of 1 bar up to 10 bar, the reaction is performed for a time within a range of from 0.5 to 3 hours.
2. The process according to claim 1, characterized in that the temperature during the reaction is adjusted within a range of from 120 to 180° C.
3. The process according to claim 1, characterized in that the formed product is dried following the reaction by further heating and applying a vacuum.
4. The process according to claim 3, characterized in that the molar ratios of calcium oxide to calcium hydroxide or calcium oxide to calcium carbonate are set to such values that the released reaction heat is sufficient to ensure drying of the product without additional input of heating energy.

* * * * *

UNITED STATES PATENT AND TRADEMARK OFFICE
CERTIFICATE OF CORRECTION

PATENT NO. : 10,239,813 B2
APPLICATION NO. : 15/737645
DATED : March 26, 2019
INVENTOR(S) : Klaus Ederle-Lerch et al.

Page 1 of 1

It is certified that error appears in the above-identified patent and that said Letters Patent is hereby corrected as shown below:

On the Title Page

Column 1, item (30) Foreign Application Priority Data:
Change "Jul. 10, 2015 (DE) .................. 10 2015 212 984" to
Jul. 10, 2015 (DE) .................. 10 2015 212 984.5

Signed and Sealed this
Thirtieth Day of April, 2019

Andrei Iancu
*Director of the United States Patent and Trademark Office*